United States Patent
Edmundson et al.

(12) 
(10) Patent No.: US 6,326,400 B1
(45) Date of Patent: *Dec. 4, 2001

(54) N-L-ALPHA-ASPARTYL-L-PHENYLALANINE 1-METHYL ESTER AND ITS DERIVATIVES FOR APPETITE ENHANCEMENT

(76) Inventors: Allen B. Edmundson, 14608 Lisa La., Edmond, OK (US) 73103; Carl V. Manion, 6313 Overcourt Manor, Oklahoma City, OK (US) 73132

(*) Notice: Subject to any disclaimer, the term of this patent is extended or adjusted under 35 U.S.C. 154(b) by 0 days.

This patent is subject to a terminal disclaimer.

(21) Appl. No.: 09/648,357

(22) Filed: Aug. 25, 2000

Related U.S. Application Data (6263) Continuation of application No. 09/385,221, filed on Aug. 27, 1999, now Pat. No. 6,156,795, which is a continuation of application No. 08/983,027, filed as application No. PCT/US96/10716 on Jun. 21, 1996, now Pat. No. 5,998,473.

(51) Int. Cl.$^7$ ........................................ A61K 31/24
(52) U.S. Cl. ............................................. 514/538
(58) Field of Search ................................. 514/538

(56) References Cited

U.S. PATENT DOCUMENTS

| | | | |
|---|---|---|---|
| 4,816,280 | 3/1989 | Billings | 426/548 |
| 4,837,036 | 6/1989 | Baker et al. | 426/43 |
| 4,856,352 | 8/1989 | Daum et al. | |
| 5,447,730 | 9/1995 | Greenleaf | 424/680 |
| 5,811,148 | 9/1998 | Chiu et al. | 426/548 |
| 5,998,473 | 12/1999 | Edmundson et al. | 514/538 |
| 6,156,795 | * 12/2000 | Edmundson et al. | 514/538 |

FOREIGN PATENT DOCUMENTS

| | | | |
|---|---|---|---|
| 3244351 | 10/1991 | (JP) | A23K/1/18 |
| 60037948 | 2/1985 | (JP) | A23L/1/236 |

* cited by examiner

*Primary Examiner*—Raymond Henley, III

(57) ABSTRACT

N-L-alpha-aspartyl-L-phenylalanine 1-methyl ester and/or its derivatives has been found have appetite-stimulating effects in vertebrate animals. Preferably, it is administered by oral ingestion of either food, beverage, or food supplement.

18 Claims, 10 Drawing Sheets

N-L-ALPHA-ASPARTYL-L-PHENYLALANINE 1-METHYL ESTER AND ITS DERIVATIVES FOR APPETITE ENHANCEMENT

CROSS REFERENCE TO RELATED APPLICATIONS

This application is a continuation of U.S. application Ser. No. 09/385,221, filed Aug. 27, 1999, now U.S. Pat. No. 6,156,795, which is a continuation of U.S. application Ser. No. 08/983,027 filed Dec. 22, 1997, now U.S. Pat. No. 5,998,473 which was the National 371, Stage of International Application No. PCT/US/96/10716, filed Jun. 21, 1996.

TECHNICAL FIELD

The present invention relates to an appetite enhancement composition and method of use.

BACKGROUND OF THE INVENTION

Pain is the most common symptom for which patients seek medical assistance. In the case of incurable diseases, treatment for pain may last for extended periods of time. Pain is both a physical and an emotional experience which differs greatly from one individual to another. Although subjective, most pain is associated with tissue damage and has a physiological basis.

Pain can be either acute or chronic. Acute pain is generally caused by sudden injury, tissue damage, or infection for which the cause is easily found. Chronic pain, however, is the pain of pathological conditions and is often difficult to isolate and treat. Chronic pain is routinely defined as pain of over six months duration.

For patients suffering from chronic pain, the autonomic nervous system adapts to the pain and evidences of autonomic hyperactivity such as tachycardia, hypertension, diaphoresis, mydriasis, and pallor disappear, leaving the physician to rely on the patient's subjective complaints in assessing chronic pain.

In the management of chronic pain, some types of pain permit treatment of the underlying disorder, i.e., radiation treatment for pain caused by bone cancer. In some cases, a particular treatment is given for a specific type of pain, i.e., treatment of trigeminal neuralgia or glossopharyngeal neuralgia with carbamazepine, reflex sympathetic dystrophies with local anesthetic, postherpetic neuralgia with direct stimulation.

In many patients, however, the pain is chronic and the physician can neither treat the underlying disturbance nor prescribe a specific therapy for that type of pain. For example, osteoarthritis is a joint disease characterized by degeneration and loss of particular cartilage and by osteophyte formation, or bony outgrowth of subchondral bone. The disease is slowly progressive, leading to chronic pain and stiffness and gradually to increasing dysfunction of the affected joint. The incidence of the disease increases with age and affects three times as many women as men.

Chronic joint pain, swelling, creaking, and stiffness are the most prominent symptoms of osteoarthritis. The disease commonly affects the distal interphalangeal joints of the hands, resulting in bone enlargements often accompanied by inflammation and pain. Weight bearing joints such as the neck, lower back, knees and hips are often affected by this type of arthritis.

Another major symptom of osteoarthritis is loss of articulation of the joint. Weakness and shrinkage of surrounding muscles may occur if pain prevents the joint from being used regularly. As movement of an affected joint becomes severely limited, the sufferer experiences loss of functionality of the joint. In the case of osteoarthritis of the hip or knees, ambulation becomes impaired.

Although osteoarthritis is the most common of the rheumatic diseases, its pathogenesis is not well understood, and currently there is no treatment that will retard or reverse pathological processes in the disease. The only treatment available to osteoarthritis sufferers has involved symptomatic treatment through analgesics for pain and nonsteroidal anti-inflammatory agents for reduction of joint inflammation. An injection of a corticosteroid may also be administered to a painful joint.

Chronic pain is also associated with multiple sclerosis (MS), also known as disseminated or insular sclerosis, a disease of the central nervous system (CNS) characterized by widespread patches of demyelination in the brain and spinal cord. The disease occurs worldwide in about 10–60 persons per 100,000 with the age at onset occurring at about 20–40 years, and appears to affect females more often than males. While MS is generally chronic and relapsing, fulminating attacks occur, and as many as 30% of the patients progress steadily from the onset.

Although multiple sclerosis is the most common demyelinating disease, its cause is unknown, and there is no treatment to retard or reverse the pathological processes of the disease. There is no specific therapy recommended because spontaneous remissions make treatment difficult to evaluate. The only treatment available to multiple sclerosis patients includes corticosteroid therapy (e.g., prednisone or dexamethasone) until manifestations remit, and symptomatic treatment such as baclofen for spasticity and pain relievers such as analgesics and opiates.

There are several types of drugs used to decrease chronic pain. Analgesics are drugs used to decrease pain without causing loss of consciousness or sensory perception. There are two basic classes of analgesics: anti-inflammatory, routinely prescribed for short-term pain relief and for modest pain, and opioids used for either short-term or long term pain relief of severe pain. The anti-inflammatory analgesics generally provide analgesia, anti-inflammation, and antipyretic action. It has been reported that the mechanism of action may be to provide inhibition of the synthesis of prostaglandins. (W. W. Douglas, "Polypeptides-angiotensin, plasma kinins, and other vasoactive agents; prostaglandins," *The Pharmacological Basis of Therapeutics*, 9th edition, L. S. Goodman and A. Gilman (eds.), MacMillan Publishing Co., Inc., New York, 1975.) Prolonged use of anti-inflammatory analgesics have been known to cause gastrointestinal problems.

The opioid analgesics, or narcotics, include all natural or synthetic chemical compounds closely related to morphine and are thought to activate one or more receptors on brain neurons. Opioid analgesics have serious side effects and thus are used with discrimination. These side effects include: 1) tolerance, which requires gradually increasing doses to maintain analgesia; 2) physical dependence, which means that the narcotics must be withdrawn gradually if they are discontinued after prolonged use; 3) constipation, which requires careful attention to bowel function, including use of stool softeners, laxatives, and enemas; and 4) various degrees of somnolence, or drowsiness, which requires adjustments in dosages and dose scheduling, or possibly varying the type of narcotic to find one better tolerated by the patient.

It has been reported that various treatments for pain are additive and should be used together rather than separately. For example, the combination of aspirin or acetaminophen and codeine is often prescribed to provide pain relief stronger than codeine by itself. Certain antidepressants prescribed for depression have been recommended as an analgesic adjuvant.

While pain management has been a problem faced by physicians for many years, available pain medications have ameliorated, but not alleviated the problem of pain treatment. A significant problem remains in that detrimental side effects are often caused by pain-relieving medications as detailed above. Thus, there remains a continuing need for alternative pain therapy regimens which would address the need for pain reduction but also reduce these side effects.

Surprisingly, it has now been discovered that N-L-alpha-aspartyl-L-phenylalanine 1-methyl ester and derivatives have appetite-stimulating properties in vertebrate animals in need of appetite stimulation.

SUMMARY OF THE INVENTION

In one aspect, the present invention relates to an animal feed comprising at least one composition of the formula

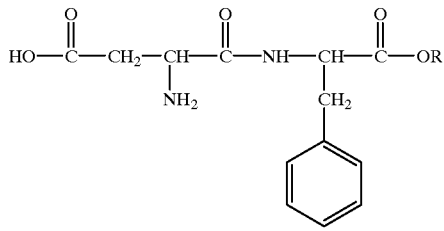

wherein R is H or an alkyl containing 1 to 6 carbons, in an effective amount per serving to stimulate the appetite of an animal consuming one serving per day of the animal feed. A preferred effective amount per serving is from about 1 to about 36 milligrams per kilogram body weight of an animal to which the feed is to be provided. A more preferred effective amount per serving is from about 3.5 to about 18 milligrams per kilogram body weight of an animal to which the feed is to be provided. A most preferred effective amount per serving is from about 2 to about 6 milligrams per kilogram body weight of an animal to which the feed is to be provided. The animal feed can be used to stimulate the appetite of a dog.

In another aspect, the present invention relates to a dog food suitable for dogs weighing from about 31.7 to about 50 kilograms, wherein a daily serving amount of the dog food comprises from about 95 to about 360 milligrams of

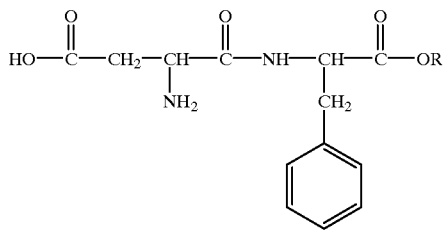

wherein R is H or an alkyl containing 1 to 6 carbons.

In another aspect, the present invention relates to a dog food suitable for dogs weighing from about 13.6 to about 31.3 kilograms, wherein a daily serving amount of the dog food comprises from about 26 to about 360 milligrams of

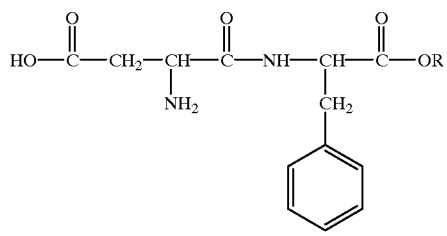

wherein R is H or an alkyl containing 1 to 6 carbons.

In yet another aspect, the present invention relates to a dog food suitable for dogs weighing from about 6.8 to about 13.2 kilograms, wherein a daily serving amount of the dog food comprises from about 13 to about 160 milligrams of

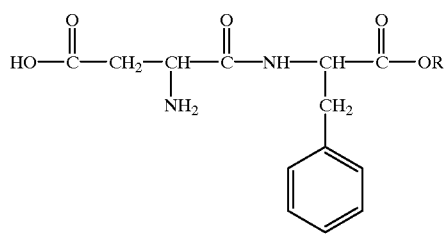

wherein R is H or an alkyl containing 1 to 6 carbons.

In yet another aspect, the present invention is a dog food suitable for dogs weighing from about 3.2 to about 6.4 kilograms, wherein a daily serving amount of the dog food comprises from about 6 to about 80 milligrams of

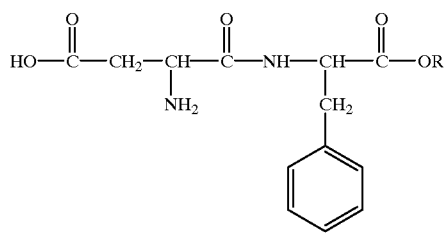

wherein R is H or an alkyl containing 1 to 6 carbons.

In yet another aspect, the present invention relates to a dog food suitable for dogs weighing from about 1.4 to about 2.8 kilograms, wherein a daily serving amount of the dog food comprises from about 3 to about 32 milligrams of

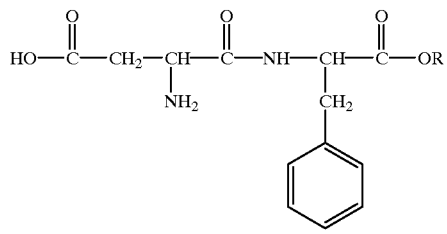

wherein R is H or an alkyl containing 1 to 6 carbons.

In yet another aspect, the present invention relates to a dietary supplement for enhancing the appetite in unit dosage form for administration to a vertebrate animal comprising at least one composition of the formula

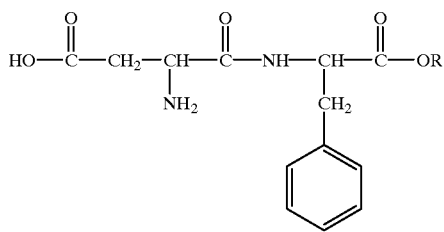

wherein R is H or an alkyl containing 1 to 6 carbons. A preferred unit dosage comprises from about 1 to about 36 milligrams per kilogram body weight of the animal. A more preferred unit dosage is from about 3.5 to about 18 milligrams per kilogram body weight of the animal. A most preferred unit dosage is from about 2 to about 6 milligrams per kilogram body weight of the animal.

In yet another aspect, the present invention relates to a method for stimulating the appetite by adding to an orally ingestible substance an appetite-stimulating amount of

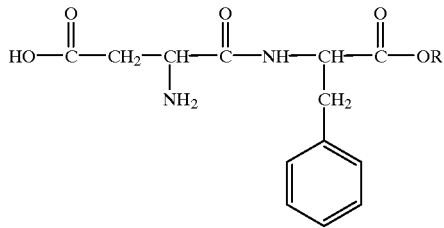

wherein R is H or an alkyl containing 1 to 6 carbons. A preferred substance is food. Another preferred substance is liquid or beverage. The appetite-stimulating amount can be a solution, spray, powder, crystal, capsule, tablets, or microencapsulated or entrapped in liposomes.

DETAILED DESCRIPTION

Figure 1:
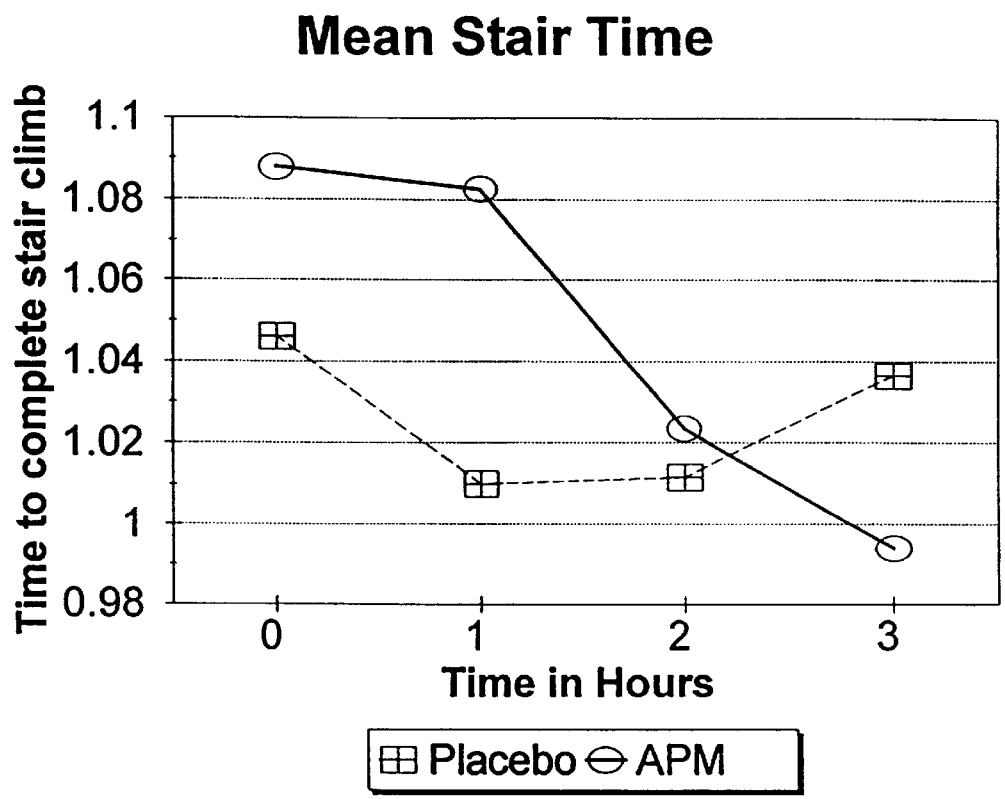
FIG. 1 is a graph depicting the average time required to ascend and descend stairs for the N-L-alpha-aspartyl-L-phenylalanine 1-methyl ester (APM) and control treatment groups measured over time.

Chronic pain has been shown to be associated with various pathological conditions such as osteoarthritis, inflammation, multiple sclerosis, and myocardial infarction. It has now been found that N-L-alpha-aspartyl-L-phenylalanine 1-methyl ester (APM), which has been sold under the trade name of ASPARTAME™ (G. D. Searle & Company, Chicago, Ill.) and its derivatives offers medicinal qualities beneficial in the treatment of chronic pain in mammals. One can use an effective amount of APM to effect a reduction in perceived pain by the recipient within one hour of dosage. An effective amount of APM which can effect pain relief after one dose is from about 80 milligrams to about 320 milligrams. A preferred range is from about 80 milligrams to about 160 milligrams. Most preferred is about 160 milligrams. The dosage can be repeated over time for continued relief, preferably at 160 milligrams every 4 hours. APM can also be administered together with other analgesics such as acetaminophen, phenacetin, aspirin, ibuprofen, phenylbutazone, indomethacin and derivatives, opiates and derivatives, piroxacam, and steroidal and nonsteroidal anti-inflammatory agents, providing additive analgesic properties.

APM can be administered orally, parenterally, intraperitoneally, or sublingually. It can be administered via ingestion of a food substance containing APM in a volume sufficient to achieve therapeutic levels. Alternatively, it can be enclosed in capsules, compressed into tablets, microencapsulated, entrapped in liposomes, in solution or suspension, alone or in combination with a substrate immobilizing material such as starch or poorly absorbable salts. Pharmaceutically compatible binding agents and/or adjuvant materials can be used as part of a composition. Tablets or capsules can contain any of the following ingredients, or compounds of similar nature: a binder such as microcrystalline cellulose, gum tragacanth or gelatin; an excipient such as starch or lactose; an integrating agent such as alginic acid or corn starch; a lubricant such as magnesium stearate; a glidant such as colloidal silicon dioxide; and additional sweetening and flavoring agents. When a capsule form is used, a liquid carrier such as a fatty oil may be used. Capsules and tablets can be coated with sugar, shellac and other enteric agents as is known. APM can also be in a controlled-release formulation.

APM is available commercially. Its preparation is also disclosed in U.S. Pat. No. 3,492,131. It is believed that various modifications can be made to the APM molecule and the resulting derivatives will also have utility in the claimed invention. Since the 1-methyl ester portion of the molecule is not believed to contribute to the analgesic activity of the molecule, N-L-alpha-aspartyl-L-phenylalanine itself or other lower alkyl esters are believed to be effective. Other possible analgesic physiologically acceptable derivatives are believed to include N-acyl-L-(beta-substituted)-aspartyl-L-phenylalanine lower alkyl esters and N-acyl-L-(beta-substituted)-aspartyl-L-phenylalanine. Chemical modifications made to the APM molecule which do not reduce the analgesic physiologically active properties disclosed herein thus fall within the scope of this invention.

Example 1

Osteoarthritis

In a well-controlled double-blind crossover study, patients suffering from osteoarthritis were given the tasks of climbing stairs, walking, and hand gripping, all of which are known to cause chronic pain in osteoarthritic patients, following treatment with either APM or a placebo. The study was performed twice for all patients, and prior to each study, all other analgesics were withheld for twenty-four hours. During the first study, one test group of eleven patients were randomly administered 4 tablets of either aspartame (76 milligrams; 19 milligrams/tablet) or placebo, and another test group of nine patients were randomly given 8 tablets of either aspartame (152 milligrams; 19 milligrams/tablet) or placebo. During the second study, each patient was given the same number of tablets but were given the opposite medication from what they had received in the first study. Following each test, data analysis of the recovered information was completed using non-parametric analyses of variance and distribution free assessments of the measured variable.

Stair Climbing

Twenty osteoarthritic patients divided into groups of nine and eleven each were asked to ascend and descend one flight of stairs, making a total of three trips with one-hour rest periods between trips. Right after the first baseline trip, patients were administered the test medication. All patients then made three subsequent trips up and down the stairs. Table I and FIG. 1 present an objective measurement of performance with respect to the time required for each patient to ascend and descend one flight of stairs. The mean results show that over time the 4-tablet APM group decreased the stair time, with a 9.6% decrease for the last trip. For the 8-tablet APM group, a decrease of 11.9% was observed for the second trip after dosing and 6.9% for the last trip. After administration of the placebo, the 4-tablet placebo group showed a decrease in stair time of 6.5% for the first and second trips after dosing, and 3.7% for the last trip. The 8-tablet placebo group showed a gradual increase in stair time with a maximum increase of 2% for the last trip.

Figure 2:
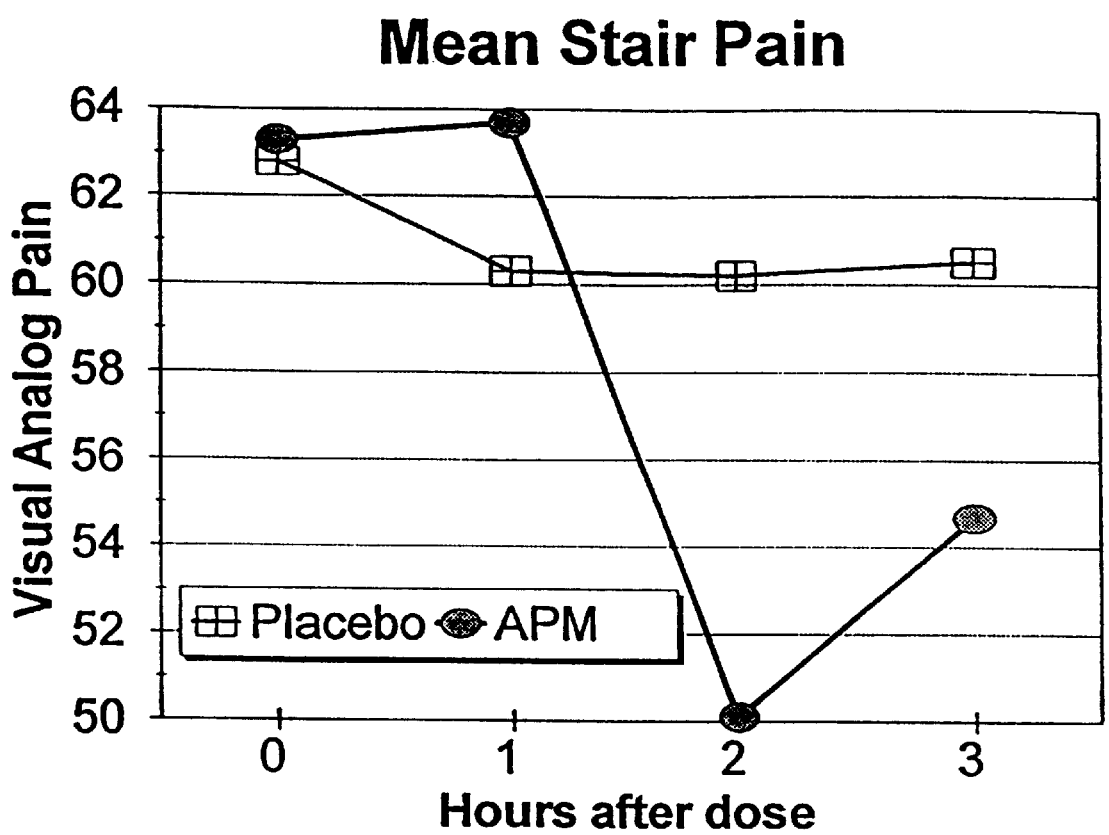
FIG. 2 is a graph depicting the average pain experienced by the APM and control treatment groups upon ascending and descending stairs measured over time.

A subjective measurement of stair pain was made by administering a visual analog pain assessment to the patients. A baseline assessment for various joints, usually three joints, was taken one hour prior to the first baseline trip, and the assessment was then repeated for each of the four trips. Each patient made an assessment under a nurse's supervision (same nurse throughout study) as to the amount of pain involved on a scale marked with increments for none, a little, more, a lot, and most. A numerical conversion of the marks on the scale in millimeters taken as the distance from the absence of pain mark was made. The representation of this assessment scale where the lower the number, the lesser the pain, and the higher the number, the greater the pain, is given in Table II and FIG. 2 as an average value for all rated joints. Referring to the mean, there was a marked decrease in the amount of pain associated with ascending and descending stairs in the APM groups in comparison to that in the placebo groups. The 4-tablet placebo group showed increased pain over the pre-climbing baseline assessment for each trip; however, while the 4-tablet APM group also experienced increased pain over the pre-climbing baseline assessment for the first two trips, they had decreased pain below or just above the pre-climbing baseline assessment for the last two trips.

TABLE I

Stair Time with and without APM

| Subject # | Stair Climb Time (min) Hours after Treatment | | | |
|---|---|---|---|---|
| | 0 | 1 | 2 | 3 |
| Control group - 4 tablets placebo | | | | |
| 1 | 1.04 | 0.59 | 0.59 | 1.01 |
| 2 | 0.92 | 0.99 | 0.97 | 0.96 |
| 3 | 1.19 | 1.12 | 1.10 | 1.15 |
| 4 | 1.00 | 1.03 | 1.04 | 1.04 |
| 5 | 0.90 | 0.91 | 0.94 | 0.98 |
| 6 | 2.09 | 1.50 | 1.51 | 1.56 |
| 7 | 0.79 | 0.79 | 0.80 | 0.81 |
| 8 | 1.28 | 1.27 | 1.23 | 1.24 |
| 9 | 1.25 | 1.26 | 1.26 | 1.26 |
| 10 | 0.72 | 1.02 | 1.01 | 0.80 |
| 11 | 0.56 | 0.58 | 0.54 | 0.55 |
| mean | 1.07 | 1.00 | 1.00 | 1.03 |
| APM group - 4 tablets APM | | | | |
| 1 | 1.05 | 1.01 | 1.00 | 1.01 |
| 2 | 0.96 | 0.96 | 0.93 | 0.88 |
| 3 | 1.10 | 1.08 | 1.04 | 1.02 |
| 4 | 1.10 | 1.10 | 1.07 | 1.06 |
| 5 | 0.90 | 0.91 | 0.89 | 0.92 |
| 6 | 2.07 | 2.10 | 2.16 | 1.54 |
| 7 | 0.78 | 0.79 | 0.79 | 0.78 |
| 8 | 1.36 | 1.30 | 1.28 | 1.33 |
| 9 | 1.23 | 1.25 | 1.24 | 1.25 |
| 10 | 1.01 | 1.02 | 1.02 | 1.02 |
| 11 | 1.07 | 1.03 | 1.01 | 0.59 |
| mean | 1.15 | 1.14 | 1.13 | 1.04 |
| Control group - 8 tablets placebo | | | | |
| 12 | 0.94 | 0.94 | 0.91 | 0.93 |
| 13 | 0.90 | 0.92 | 0.90 | 0.96 |
| 14 | 1.44 | 1.43 | 1.51 | 1.56 |
| 15 | 0.49 | 0.51 | 0.54 | 0.58 |
| 16 | 1.24 | 1.25 | 1.25 | 1.22 |
| 17 | 1.07 | 1.07 | 1.13 | 1.13 |
| 18 | 1.14 | 1.11 | 1.09 | 1.10 |
| 19 | 0.81 | 0.84 | 0.83 | 0.84 |
| 20 | 1.15 | 1.08 | 1.08 | 1.05 |
| mean | 1.02 | 1.02 | 1.03 | 1.04 |
| APM group - 8 tablets APM | | | | |
| 12 | 0.94 | 0.92 | 0.89 | 0.86 |
| 13 | 0.87 | 0.88 | 0.89 | 0.90 |
| 14 | 1.45 | 1.42 | 1.35 | 1.44 |
| 15 | 0.50 | 0.55 | 0.56 | 0.51 |
| 16 | 1.33 | 1.25 | 1.27 | 1.25 |
| 17 | 1.00 | 1.03 | 0.55 | 0.59 |
| 18 | 1.14 | 1.16 | 1.08 | 1.08 |
| 19 | 0.84 | 0.88 | 0.86 | 0.83 |
| 20 | 1.06 | 1.02 | 0.58 | 1.00 |
| mean | 1.01 | 1.01 | 0.89 | 0.94 |
| Total mean score by treatment group | | | | |
| Control | 1.05 | 1.01 | 1.01 | 1.04 |
| APM | 1.09 | 1.08 | 1.02 | 0.99 |

TABLE II

Stair Pain with and without APM

| Subject # | Stair Pain (relative numerical scale) Hours after Treatment | | | | |
|---|---|---|---|---|---|
| | −1 | 0 | 1 | 2 | 3 |
| Control group - 4 tablets placebo | | | | | |
| 1 | 27 | 49 | 33 | 42 | 36 |

TABLE II-continued

Stair Pain with and without APM

Stair Pain (relative numerical scale)
Hours after Treatment

| Subject # | −1 | 0 | 1 | 2 | 3 |
|---|---|---|---|---|---|
| 2 | 62 | 102 | 119 | 91 | 74 |
| 3 | 51 | 85 | 67 | 110 | 73 |
| 4 | 31 | 73 | 25 | 32 | 31 |
| 5 | 42 | 59 | 38 | 73 | 58 |
| 6 | 93 | 117 | 118 | 126 | 127 |
| 7 | 24 | 81 | 97 | 89 | 88 |
| 8 | 41 | 22 | 31 | 28 | 21 |
| 9 | 31 | 46 | 64 | 45 | 75 |
| 10 | 55 | 72 | 78 | 88 | 85 |
| 11 | 36 | 48 | 50 | 31 | 36 |
| mean | 44.82 | 68.55 | 65.45 | 68.64 | 64.00 |
| APM group - 4 tablets APM | | | | | |
| 1 | 45 | 47 | 48 | 36 | 22 |
| 2 | 24 | 80 | 91 | 32 | 38 |
| 3 | 106 | 130 | 130 | 73 | 73 |
| 4 | 79 | 63 | 70 | 40 | 42 |
| 5 | 41 | 71 | 56 | 56 | 44 |
| 6 | 46 | 95 | 130 | 101 | 130 |
| 7 | 28 | 87 | 87 | 56 | 74 |
| 8 | 59 | 28 | 30 | 28 | 62 |
| 9 | 94 | 56 | 47 | 30 | 30 |
| 10 | 67 | 83 | 96 | 91 | 105 |
| 11 | 36 | 45 | 49 | 52 | 24 |
| mean | 56.82 | 71.36 | 75.82 | 54.09 | 58.55 |
| Control group - 8 tablets placebo | | | | | |
| 12 | 33 | 66 | 60 | 51 | 59 |
| 13 | 22 | 40 | 26 | 30 | 24 |
| 14 | 35 | 74 | 115 | 116 | 118 |
| 15 | 45 | 74 | 21 | 33 | 50 |
| 16 | 50 | 52 | 50 | 51 | 56 |
| 17 | 22 | 28 | 26 | 22 | 21 |
| 18 | 62 | 74 | 92 | 77 | 74 |
| 19 | 8 | 49 | 63 | 49 | 83 |
| 20 | 43 | 45 | 33 | 20 | 21 |
| mean | 35.56 | 55.78 | 54.00 | 49.89 | 56.22 |
| APM group - 8 tablets APM | | | | | |
| 12 | 42 | 72 | 71 | 51 | 53 |
| 13 | 31 | 31 | 39 | 31 | 31 |
| 14 | 69 | 97 | 84 | 85 | 117 |
| 15 | 33 | 35 | 23 | 31 | 33 |
| 16 | 53 | 52 | 54 | 53 | 54 |
| 17 | 39 | 31 | 15 | 21 | 17 |
| 18 | 25 | 48 | 65 | 49 | 56 |
| 19 | 57 | 78 | 63 | 72 | 74 |
| 20 | 34 | 37 | 26 | 14 | 14 |
| mean | 42.56 | 53.44 | 48.89 | 45.22 | 49.89 |
| Total mean score by treatment group | | | | | |
| Control | 40.65 | 62.80 | 60.30 | 60.20 | 60.50 |
| APM | 50.40 | 63.30 | 63.70 | 50.10 | 54.65 |

Table III provides pain assessment measurements for the most sensitive joint for some of the patients taken at one hour and two hours after treatment. For the 4-tablet treatment groups, the placebo group showed a slight increase in pain (2.2%), while the APM group experienced a 52.2% decrease in pain. The 8-tablet APM group also experienced a significant decrease in pain (48.2%), compared to a 24.5% decrease in pain for the 8-tablet placebo group.

Figure 3:
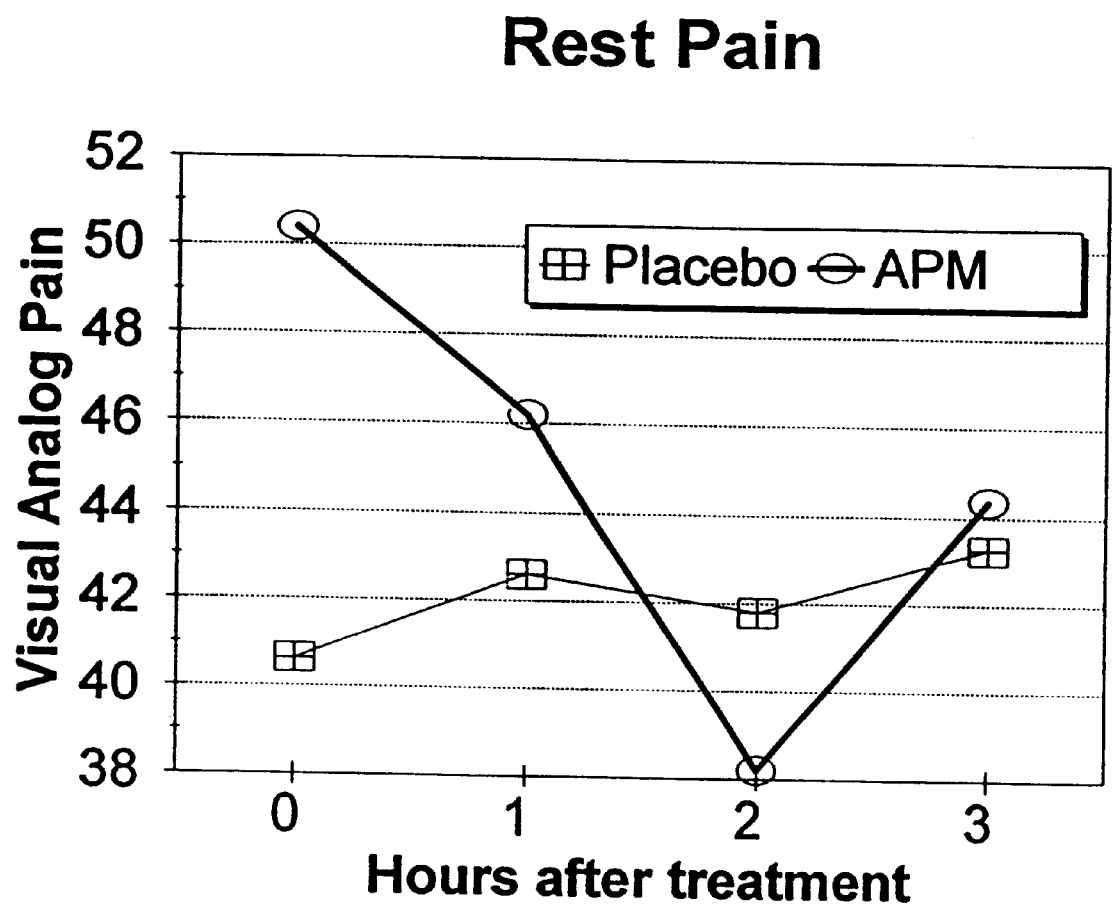
FIG. 3 is a graph depicting the average rest pain experienced by the APM and control treatment groups taken after a one hour rest period following ascending and descending stairs measured over time.
Figure 4:
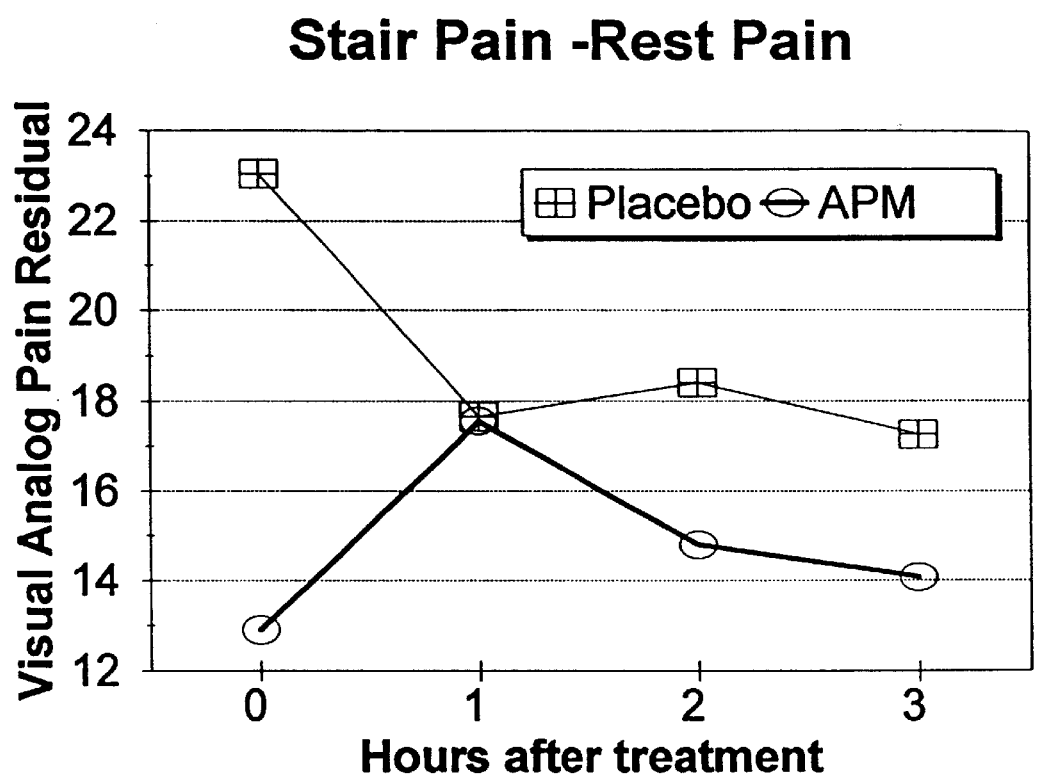
FIG. 4 is a graph depicting the difference between stair pain and rest pain experienced by the APM and control treatment groups upon ascending and descending stairs measured over time.

An evaluation of pain was also measured using the visual analog pain assessment method by the patient at the end of each rest period (Table IV and FIG. 3). While the average rest pain generally increased for both placebo groups, the 4-tablet APM group experienced a 12.2%, 16.5%, and 10.4% decrease in rest pain from pretreatment over time, while the 8-tablet APM group, a 2.3%, 36.8% and 14.6% decrease. In Table V and FIG. 4, the mean difference between stair pain and rest pain for each patient at each time period is given, showing that the mean difference of the APM groups was lower than the placebo groups. As indicated by the negative numbers, some patients in both groups experienced greater rest pain than stair climb pain.

Walking Distance

Figure 5:
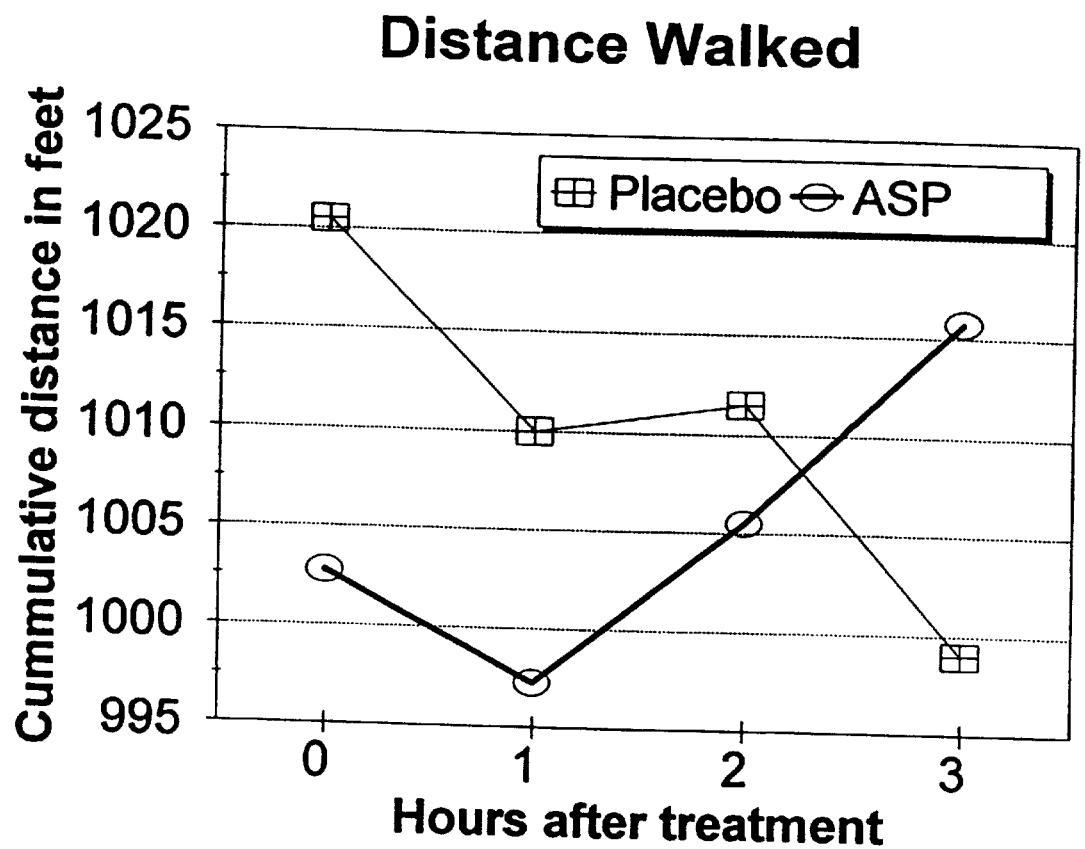
FIG. 5 is a graph depicting the average distance walked by the APM and control treatment groups measured over time.

Chronic pain was examined in respect to distance walking at a comfortable speed for a five minute period. A pre-walking baseline pain assessment was performed. After establishing a baseline walking distance, the 4- and 8-tablet APM groups were given 76 milligrams and 152 milligrams APM, respectively, while the 4- and 8-tablet control groups were given the appropriate number of placebo tablets. After resting for one hour, the patients repeated the 5-minute walking procedure three times with one hour rest periods between trips. Table VI and FIG. 5 show the total distance walked in terms of feet traveled. The average distance walked in the control groups decreased slightly over time, with the mean varying from −0.5% to −2.2% from baseline. Comparatively, the average distance walked in the APM groups varied from −0.4% to 1.8% from baseline. Although the average distance walked decreased at one hour from baseline, there was an increase at 3 hours from baseline for both APM groups.

TABLE III

Stair Pain of Most Sensitive Joint with and without APM

Stair Pain (relative numerical scale) Hours after Treatment

| Subject # | 1 | 2 |
|---|---|---|
| Control group - 4 tablets placebo | | |
| 1 | 24 | 43 |
| 2 | 113 | 105 |
| 3 | 63 | 92 |
| 4 | 25 | 32 |
| 5 | 21 | 57 |
| 6 | 149 | 149 |
| 7 | 97 | 77 |
| 8 | 16 | 21 |
| 9 | 73 | 35 |
| 10 | — | — |
| 11 | 33 | 17 |
| mean | 61.40 | 62.80 |
| APM group - 4 tablets APM | | |
| 1 | 53 | 35 |
| 2 | 107 | 53 |
| 3 | 130 | 16 |
| 4 | 104 | 46 |
| 5 | 56 | 22 |
| 6 | 150 | 106 |
| 7 | 75 | 39 |
| 8 | 45 | 26 |
| 9 | 73 | 37 |
| 10 | — | — |
| 11 | 32 | 14 |
| mean | 82.50 | 39.40 |
| Control group - 8 tablets placebo | | |
| 12 | 48 | 39 |
| 13 | 26 | 38 |
| 14 | — | — |
| 15 | — | — |
| 16 | — | — |
| 17 | — | — |
| 18 | 129 | 93 |

TABLE III-continued

Stair Pain of Most Sensitive Joint with and without APM

| Subject # | Stair Pain (relative numerical scale) Hours after Treatment | |
|---|---|---|
| | 1 | 2 |
| 19 | 86 | 58 |
| 20 | 33 | 15 |
| mean | 64.40 | 48.60 |
| APM group - 8 tablets APM | | |
| 12 | 71 | 11 |
| 13 | 55 | 39 |
| 14 | — | — |
| 15 | — | — |
| 16 | — | — |
| 17 | — | — |
| 18 | 32 | 15 |
| 19 | 86 | 72 |
| 20 | 36 | 8 |
| mean | 56.00 | 29.00 |
| Total mean score by treatment group | | |
| Control | 62.40 | 58.07 |
| APM | 73.67 | 35.93 |

TABLE IV

Rest Pain with and without APM

| Subject # | Rest Pain (relative numerical scale) Hours after Treatment | | | |
|---|---|---|---|---|
| | 0 | 1 | 2 | 3 |
| Control group - 4 tablets placebo | | | | |
| 1 | 27 | 31 | 32 | 45 |
| 2 | 62 | 79 | 36 | 48 |
| 3 | 51 | 10 | 30 | 15 |
| 4 | 31 | 46 | 30 | 30 |
| 5 | 42 | 54 | 40 | 41 |
| 6 | 93 | 116 | 127 | 129 |
| 7 | 24 | 39 | 42 | 40 |
| 8 | 41 | 35 | 23 | 16 |
| 9 | 31 | 31 | 48 | 58 |
| 10 | 55 | 70 | 73 | 80 |
| 11 | 36 | 35 | 32 | 25 |
| mean | 44.82 | 49.64 | 46.64 | 47.91 |
| APM group - 4 tablets APM | | | | |
| 1 | 45 | 37 | 45 | 17 |
| 2 | 24 | 50 | 77 | 78 |
| 3 | 106 | 25 | 14 | 30 |
| 4 | 79 | 68 | 56 | 40 |
| 5 | 41 | 40 | 39 | 41 |
| 6 | 46 | 77 | 94 | 99 |
| 7 | 28 | 9 | 8 | 39 |
| 8 | 59 | 49 | 25 | 27 |
| 9 | 94 | 77 | 32 | 24 |
| 10 | 67 | 80 | 89 | 96 |
| 11 | 36 | 38 | 43 | 69 |
| mean | 56.82 | 50.00 | 47.45 | 50.91 |
| Control group - 8 tablets placebo | | | | |
| 12 | 33 | 34 | 16 | 14 |
| 13 | 22 | 24 | 28 | 32 |
| 14 | 35 | 78 | 115 | 118 |
| 15 | 45 | 19 | 32 | 32 |
| 16 | 50 | 53 | 50 | 50 |
| 17 | 22 | 19 | 18 | 24 |
| 18 | 62 | 35 | 30 | 34 |
| 19 | 8 | 8 | 8 | 10 |
| 20 | 43 | 36 | 26 | 24 |

TABLE IV-continued

Rest Pain with and without APM

| Subject # | Rest Pain (relative numerical scale) Hours after Treatment | | | |
|---|---|---|---|---|
| | 0 | 1 | 2 | 3 |
| mean | 35.56 | 34.00 | 35.89 | 37.56 |
| APM group - 8 tablets APM | | | | |
| 12 | 42 | 58 | 32 | 38 |
| 13 | 31 | 32 | 28 | 33 |
| 14 | 69 | 73 | 53 | 86 |
| 15 | 33 | 20 | 19 | 27 |
| 16 | 53 | 54 | 52 | 52 |
| 17 | 39 | 35 | 20 | 16 |
| 18 | 25 | 33 | 12 | 20 |
| 19 | 57 | 39 | 9 | 39 |
| 20 | 34 | 30 | 17 | 16 |
| mean | 42.56 | 41.56 | 26.89 | 36.33 |
| Total mean score by treatment group | | | | |
| Control | 40.65 | 42.60 | 41.80 | 43.25 |
| APM | 50.40 | 46.20 | 38.20 | 44.35 |

TABLE V

Stair Pain v. Rest Pain with and without APM

| Subject # | Stair Pain Minus Rest Pain Hours after Treatment | | | |
|---|---|---|---|---|
| | 0 | 1 | 2 | 3 |
| Control groups - 4 or 8 tablets placebo | | | | |
| 1 | 22 | 1 | 10 | −9 |
| 2 | 40 | 40 | 55 | 26 |
| 3 | 34 | 57 | 80 | 58 |
| 4 | 42 | −21 | 2 | 1 |
| 5 | 17 | −16 | 33 | 17 |
| 6 | 24 | 2 | −1 | −2 |
| 7 | 57 | 58 | 47 | 48 |
| 8 | −19 | −4 | 5 | 5 |
| 9 | 15 | 33 | −3 | 17 |
| 10 | 17 | 8 | 15 | 5 |
| 11 | 12 | 15 | −1 | 11 |
| 12 | 33 | 26 | 35 | 45 |
| 13 | 18 | 2 | 2 | −8 |
| 14 | 39 | 37 | 1 | 0 |
| 15 | 29 | 2 | 1 | 18 |
| 16 | 20 | −3 | 1 | 6 |
| 17 | 6 | 7 | 4 | −3 |
| 18 | 12 | 57 | 47 | 40 |
| 19 | 41 | 55 | 41 | 73 |
| 20 | 2 | −3 | −6 | −3 |
| mean | 23.05 | 17.65 | 18.40 | 17.25 |
| APM groups - 4 or 8 tablets APM | | | | |
| 1 | 2 | 11 | −9 | 5 |
| 2 | 56 | 41 | −45 | −40 |
| 3 | 24 | 105 | 59 | 43 |
| 4 | −16 | 2 | −16 | 2 |
| 5 | 30 | 16 | 17 | 3 |
| 6 | 49 | 53 | 7 | 31 |
| 7 | 59 | 78 | 48 | 35 |
| 8 | −31 | −19 | −2 | 35 |
| 9 | −38 | −30 | −2 | −4 |
| 10 | 16 | 16 | 2 | 9 |
| 11 | 9 | 11 | 9 | −45 |
| 12 | 30 | 13 | 19 | 15 |
| 13 | 0 | 7 | 3 | −2 |
| 14 | 28 | 11 | 84 | 116 |
| 15 | 2 | 3 | 12 | 6 |
| 16 | −1 | 0 | 1 | 2 |
| 17 | −8 | −20 | 1 | 1 |

TABLE V-continued

Stair Pain v. Rest Pain with and without APM

| | Stair Pain Minus Rest Pain Hours after Treatment | | | |
|---|---|---|---|---|
| Subject # | 0 | 1 | 2 | 3 |
| 18 | 23 | 32 | 37 | 36 |
| 19 | 21 | 25 | 74 | 35 |
| 20 | 3 | −4 | −3 | −2 |
| mean | 12.90 | 17.55 | 14.78 | 14.06 |

Figure 6:
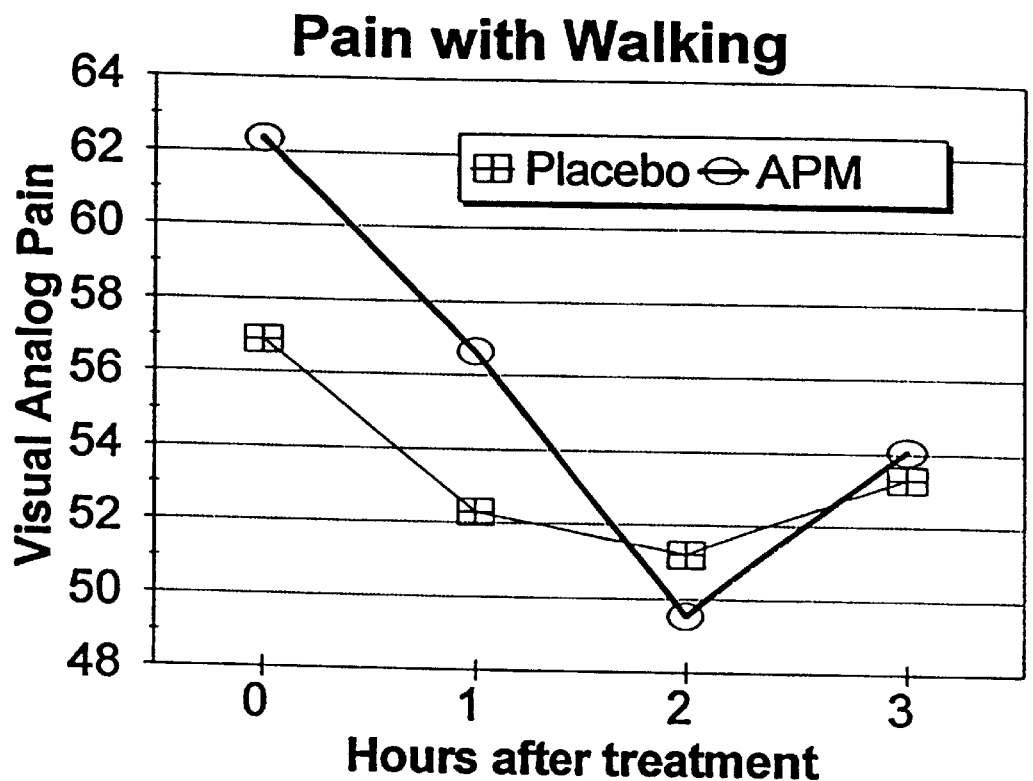
FIG. 6 is a graph depicting the average pain experienced by the APM and control treatment groups upon walking for five minutes measured over time.

Walking distance pain was recorded via the visual analog pain assessment. A baseline assessment was taken one hour prior to the first baseline trip. The assessment was then repeated for each of the four trips. A relative numerical representation of this assessment scale where the lower the number the lesser the pain, and the higher the number, the greater the pain, is given in Table VII and FIG. 6. The average distance pain after the four walks increased over the pre-walking baseline assessment by 22.7 to 42.8% for the 4-tablet control group, and 20.6% to 35.6% for the 8-tablet control group. Comparatively, the patients in the 4-tablet APM group showed an increase in average distance pain after the baseline walk (23.0%) and the first walk after dosing (21.8%), while the average distance pain decreased below the pre-walking baseline assessment by 1.1% after the second walk after dosing and then increased to 11.4% above the pre-walking baseline assessment after the last walk. For the 8-tablet APM group, the average distance pain after the baseline walk increased over the pre-walking assessment by 24.8%; however, the average distance pain for the remaining three walks was right at or below the pre-walking baseline assessment.

TABLE VI

Walking Distance with and without APM

| | Walking Distance (feet) Hours after Treatment | | | |
|---|---|---|---|---|
| Subject # | 0 | 1 | 2 | 3 |
| Control group - 4 tablets placebo | | | | |
| 1 | 1035 | 1040 | 1055 | 1045 |
| 2 | 895 | 875 | 895 | 825 |
| 3 | 1000 | 980 | 1030 | 1000 |
| 4 | 1010 | 980 | 970 | 990 |
| 5 | 1100 | 1095 | 1095 | 1120 |
| 6 | 800 | 775 | 810 | 800 |
| 7 | 1325 | 1295 | 1310 | 1295 |
| 8 | 865 | 900 | 920 | 890 |
| 9 | 840 | 865 | 850 | 810 |
| 10 | 1175 | 1110 | 1085 | 1100 |
| 11 | 1150 | 1125 | 1105 | 1100 |
| mean | 1017.73 | 1003.64 | 1011.36 | 997.73 |
| APM group - 4 tablets APM | | | | |
| 1 | 990 | 1000 | 1000 | 1000 |
| 2 | 880 | 840 | 835 | 870 |
| 3 | 1025 | 1080 | 1090 | 1100 |
| 4 | 910 | 885 | 900 | 910 |
| 5 | 1075 | 1075 | 1070 | 1060 |
| 6 | 755 | 770 | 785 | 810 |
| 7 | 1320 | 1320 | 1325 | 1310 |
| 8 | 820 | 825 | 890 | 885 |
| 9 | 830 | 810 | 850 | 880 |
| 10 | 1300 | 1235 | 1245 | 1220 |
| 11 | 1010 | 1000 | 1025 | 1070 |
| mean | 992.27 | 985.45 | 1001.36 | 1010.45 |

TABLE VI-continued

Walking Distance with and without APM

| | Walking Distance (feet) Hours after Treatment | | | |
|---|---|---|---|---|
| Subject # | 0 | 1 | 2 | 3 |
| Control group - 8 tablets placebo | | | | |
| 12 | 935 | 930 | 920 | 910 |
| 13 | 1150 | 1160 | 1445 | 1120 |
| 14 | 780 | 785 | 760 | 770 |
| 15 | 1230 | 1250 | 1240 | 1170 |
| 16 | 900 | 930 | 940 | 920 |
| 17 | 1065 | 1025 | 995 | 1000 |
| 18 | 1095 | 1070 | 1085 | 1120 |
| 19 | 1350 | 1305 | 1300 | 1260 |
| 20 | 710 | 705 | 720 | 735 |
| mean | 1023.89 | 1017.78 | 1011.67 | 1000.56 |
| APM group - 8 tablets APM | | | | |
| 12 | 980 | 930 | 910 | 1000 |
| 13 | 1120 | 1140 | 1115 | 1120 |
| 14 | 790 | 795 | 825 | 740 |
| 15 | 1210 | 1270 | 1260 | 1260 |
| 16 | 890 | 900 | 925 | 905 |
| 17 | 1000 | 995 | 960 | 1045 |
| 18 | 1075 | 1060 | 1070 | 1100 |
| 19 | 1285 | 1250 | 1250 | 1250 |
| 20 | 790 | 765 | 780 | 780 |
| mean | 1015.56 | 1011.67 | 1010.56 | 1022.22 |
| Total mean score by treatment group | | | | |
| Control | 1020.50 | 1010.00 | 1011.50 | 999.00 |
| APM | 1002.75 | 997.25 | 1005.50 | 1015.75 |

TABLE VII

Walking Pain with and without APM

| | Walking Pain (relative numerical scale) Hours after Treatment | | | | |
|---|---|---|---|---|---|
| Subject # | −1 | 0 | 1 | 2 | 3 |
| Control group - 4 tablets placebo | | | | | |
| 1 | 27 | 43 | 49 | 43 | 37 |
| 2 | 62 | 81 | 80 | 53 | 53 |
| 3 | 51 | 83 | 25 | 16 | 53 |
| 4 | 31 | 46 | 38 | 22 | 22 |
| 5 | 42 | 87 | 87 | 71 | 39 |
| 6 | 93 | 95 | 116 | 128 | 128 |
| 7 | 24 | 57 | 57 | 77 | 76 |
| 8 | 41 | 63 | 43 | 35 | 56 |
| 9 | 31 | 39 | 57 | 56 | 65 |
| 10 | 55 | 70 | 70 | 70 | 73 |
| 11 | 36 | 40 | 38 | 34 | 33 |
| mean | 44.82 | 64.00 | 60.00 | 55.00 | 57.73 |
| APM group - 4 tablets APM | | | | | |
| 1 | 45 | 60 | 53 | 33 | 35 |
| 2 | 24 | 50 | 62 | 42 | 99 |
| 3 | 106 | 118 | 94 | 32 | 13 |
| 4 | 79 | 51 | 63 | 54 | 59 |
| 5 | 41 | 71 | 71 | 73 | 74 |
| 6 | 46 | 81 | 93 | 100 | 100 |
| 7 | 28 | 58 | 40 | 37 | 42 |
| 8 | 59 | 71 | 86 | 65 | 85 |
| 9 | 94 | 83 | 49 | 29 | 30 |
| 10 | 67 | 74 | 86 | 90 | 100 |
| 11 | 36 | 52 | 64 | 63 | 59 |
| mean | 56.82 | 69.91 | 69.18 | 56.18 | 63.27 |
| Control group - 8 tablets placebo | | | | | |
| 12 | 33 | 68 | 17 | 21 | 18 |
| 13 | 22 | 29 | 43 | 57 | 47 |

TABLE VII-continued

Walking Pain with and without APM

Walking Pain (relative numerical scale)
Hours after Treatment

| Subject # | −1 | 0 | 1 | 2 | 3 |
|---|---|---|---|---|---|
| 14 | 35 | 55 | 95 | 114 | 114 |
| 15 | 45 | 75 | 32 | 49 | 55 |
| 16 | 50 | 51 | 60 | 61 | 72 |
| 17 | 22 | 26 | 27 | 30 | 28 |
| 18 | 62 | 87 | 52 | 59 | 42 |
| 19 | 8 | 8 | 41 | 8 | 38 |
| 20 | 43 | 35 | 19 | 20 | 17 |
| mean | 35.56 | 48.22 | 42.89 | 46.56 | 47.89 |
| APM group - 8 tablets APM | | | | | |
| 12 | 42 | 41 | 30 | 40 | 40 |
| 13 | 31 | 47 | 48 | 47 | 46 |
| 14 | 69 | 95 | 84 | 84 | 96 |
| 15 | 33 | 38 | 31 | 36 | 27 |
| 16 | 53 | 54 | 61 | 54 | 56 |
| 17 | 39 | 35 | 28 | 27 | 24 |
| 18 | 25 | 49 | 55 | 29 | 44 |
| 19 | 57 | 75 | 11 | 40 | 39 |
| 20 | 34 | 44 | 24 | 16 | 13 |
| mean | 42.56 | 53.11 | 41.33 | 41.44 | 42.78 |
| Total mean score by treatment group | | | | | |
| Control | 40.65 | 56.90 | 52.30 | 51.20 | 53.30 |
| APM | 50.40 | 62.35 | 56.65 | 49.55 | 54.05 |

Grip Strength

Figure 7:
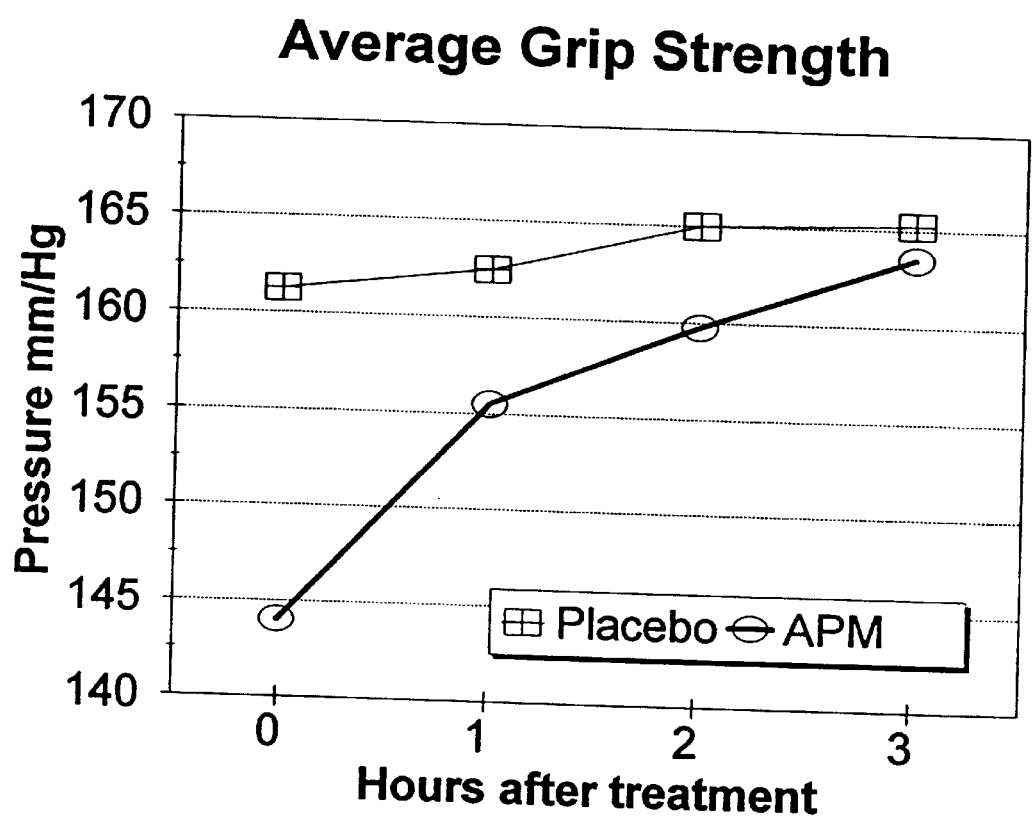
FIG. 7 is a graph depicting the average grip strength for the APM and control treatment groups measured over time.

Grip strength was measured by placing the cuff into a cloth bag and filling with air to a resting pressure of 20 mmHg for easy gripping. Each patient gripped the cloth bag, and the increase in pressure registered as change in mmHg on the cuff was recorded. Following a baseline gripping measurement, the 4- and 8-tablet APM groups were given 76 milligrams and 152 milligrams APM, respectively, while the 4- and 8-tablet control groups were given the appropriate number of placebo tablets. After a one hour rest period, the gripping measurement was repeated three more times with a one hour rest period between each measurement. As shown in Table VIII and FIG. 7, both APM groups and the 4-tablet control group basically showed increasing grip strength over time. The 8-tablet control varied about 2% to 3% above and below baseline.

Figure 8:
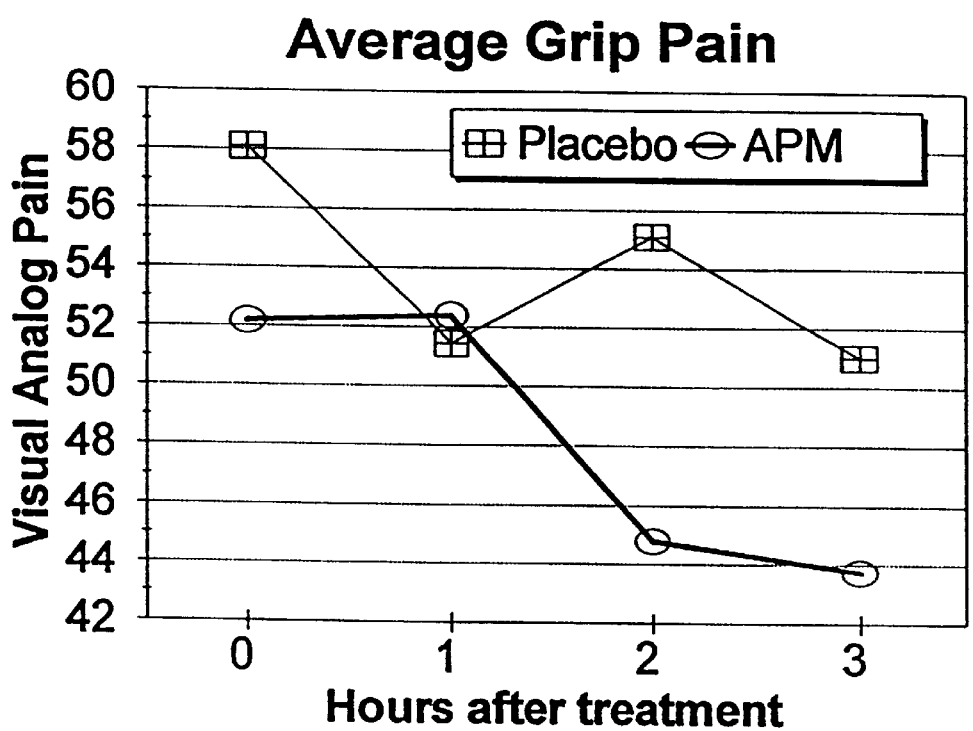
FIG. 8 is a graph depicting the average gripping pain experienced by the APM and control treatment groups measured over time.

To determine average grip pain, a visual analog pain assessment was performed prior to the baseline gripping measurement and then repeated after each subsequent gripping measurement. In Table IX and FIG. 8, the mean data shows that within 2 hours after treatment, grip pain for both APM groups fell at or below the pre-gripping baseline assessment, while both control groups stayed at least 8% higher than the pre-gripping baseline assessment.

TABLE VIII

Grip Strength with and without APM

Grip Strength (mmHg)
Hours after Treatment

| Subject # | 0 | 1 | 2 | 3 |
|---|---|---|---|---|
| Control group - 4 tablets placebo | | | | |
| 1 | 275 | 280 | 265 | 260 |
| 2 | 135 | 110 | 105 | 105 |
| 3 | 175 | 170 | 180 | 170 |
| 4 | 165 | 180 | 160 | 170 |
| 5 | 170 | 195 | 195 | 180 |
| 6 | 140 | 155 | 145 | 200 |
| 7 | 95 | 80 | 95 | 95 |
| 8 | 225 | 235 | 245 | 275 |
| 9 | 195 | 205 | 205 | 245 |
| 10 | 230 | 230 | 235 | 225 |
| 11 | 155 | 160 | 145 | 160 |
| mean | 178.18 | 181.82 | 179.55 | 189.67 |
| APM group - 4 tablets APM | | | | |
| 1 | 240 | 235 | 255 | 250 |
| 2 | 65 | 85 | 80 | 105 |
| 3 | 75 | 135 | 155 | 180 |
| 4 | 115 | 135 | 165 | 145 |
| 5 | 140 | 165 | 170 | 160 |
| 6 | 120 | 100 | 140 | 160 |
| 7 | 95 | 110 | 95 | 105 |
| 8 | 190 | 240 | 215 | 210 |
| 9 | 270 | 275 | 295 | 265 |
| 10 | 170 | 165 | 155 | 155 |
| 11 | 180 | 170 | 170 | 170 |
| mean | 150.91 | 165.00 | 172.27 | 173.18 |
| Control group - 8 tablets placebo | | | | |
| 12 | 85 | 90 | 100 | 100 |
| 13 | 155 | 155 | 170 | 160 |
| 14 | 165 | 160 | 145 | 135 |
| 15 | 150 | 140 | 145 | 140 |
| 16 | 230 | 210 | 210 | 215 |
| 17 | 180 | 180 | 190 | 225 |
| 18 | 165 | 150 | 170 | 165 |
| 19 | 85 | 90 | 105 | 85 |
| 20 | 55 | 75 | 90 | 90 |
| mean | 141.11 | 138.89 | 147.22 | 146.11 |
| APM group - 8 tablets APM | | | | |
| 12 | 80 | 90 | 95 | 95 |
| 13 | 145 | 160 | 160 | 165 |
| 14 | 125 | 125 | 120 | 135 |
| 15 | 155 | 165 | 165 | 170 |
| 16 | 235 | 230 | 220 | 225 |
| 17 | 185 | 190 | 195 | 220 |
| 18 | 110 | 130 | 160 | 180 |
| 19 | 110 | 115 | 100 | 95 |
| 20 | 75 | 90 | 85 | 80 |
| mean | 135.56 | 143.89 | 144.44 | 151.67 |
| Total mean score by treatment group | | | | |
| Control | 161.50 | 162.50 | 165.00 | 170.00 |
| APM | 144.00 | 155.50 | 159.75 | 163.50 |

TABLE IX

Grip Pain with and without APM

Grip Pain (relative numerical scale)
Hours after Treatment

| Subject # | −1 | 0 | 1 | 2 | 3 |
|---|---|---|---|---|---|
| Control group - 4 tablets placebo | | | | | |
| 1 | 48 | 79 | 50 | 59 | 51 |
| 2 | — | — | — | — | — |
| 3 | 85 | 25 | 22 | 84 | 84 |
| 4 | 46 | 59 | 21 | 21 | 15 |
| 5 | — | — | — | — | — |
| 6 | 47 | 82 | 105 | 86 | 82 |

TABLE IX-continued

Grip Pain with and without APM

| | Grip Pain (relative numerical scale) Hours after Treatment | | | | |
|---|---|---|---|---|---|
| Subject # | −1 | 0 | 1 | 2 | 3 |
| 7 | 75 | 76 | 76 | 100 | 77 |
| 8 | 19 | 19 | 18 | 17 | 16 |
| 9 | 24 | 42 | 42 | 41 | 25 |
| 10 | 43 | 70 | 80 | 87 | 85 |
| 11 | 37 | 54 | 45 | 35 | 45 |
| mean | 47.11 | 56.22 | 51.00 | 58.89 | 53.33 |
| APM group - 4 tablets APM | | | | | |
| 1 | 17 | 45 | 55 | 22 | 19 |
| 2 | — | — | — | — | — |
| 3 | 106 | 106 | 40 | 20 | 10 |
| 4 | 47 | 49 | 33 | 30 | 35 |
| 5 | — | — | — | — | — |
| 6 | 46 | 82 | 106 | 105 | 93 |
| 7 | 40 | 58 | 75 | 75 | 73 |
| 8 | 16 | 19 | 19 | 20 | 17 |
| 9 | 41 | 42 | 23 | 24 | 22 |
| 10 | 71 | 81 | 91 | 95 | 107 |
| 11 | 50 | 53 | 59 | 50 | 63 |
| mean | 48.22 | 59.44 | 55.67 | 49.00 | 48.78 |
| Control group - 8 tablets placebo | | | | | |
| 12 | 16 | 48 | 46 | 38 | 17 |
| 13 | 23 | 49 | 36 | 23 | 51 |
| 14 | 35 | 71 | 92 | 132 | 97 |
| 15 | 64 | 66 | 27 | 32 | 57 |
| 16 | 48 | 47 | 47 | 48 | 51 |
| 17 | 14 | 8 | 11 | 8 | 8 |
| 18 | 103 | 128 | 94 | 101 | 84 |
| 19 | 41 | 72 | 73 | 40 | 57 |
| 20 | 43 | 51 | 41 | 40 | 16 |
| mean | 43.00 | 60.00 | 51.89 | 51.33 | 48.67 |
| APM group - 8 tablets APM | | | | | |
| 12 | 16 | 43 | 74 | 39 | 15 |
| 13 | 23 | 23 | 22 | 20 | 20 |
| 14 | 34 | 31 | 71 | 71 | 72 |
| 15 | 32 | 35 | 40 | 48 | 56 |
| 16 | 18 | 17 | 16 | 20 | 17 |
| 17 | 9 | 13 | 21 | 24 | 7 |
| 18 | 88 | 75 | 90 | 47 | 71 |
| 19 | 98 | 97 | 72 | 74 | 73 |
| 20 | 75 | 70 | 36 | 22 | 17 |
| mean | 43.67 | 44.89 | 49.11 | 40.56 | 38.67 |
| Total mean score by treatment group | | | | | |
| Control | 45.06 | 58.11 | 51.44 | 55.11 | 51.00 |
| APM | 45.94 | 52.17 | 52.39 | 44.78 | 43.72 |

Overall, this study documents that use of APM was successful in relieving pain and that performance was measurably improved. Statistical assessments of measured variables suggests that the inference that the observed differences were due to chance is improbable at $p<0.05$ to $p<0.01$ or more.

Example 2

Osteoarthritis—Pain Alleviation

The analgesic properties of APM given over time was demonstrated in one osteoarthritic patient engaged in viewing a football game. The patient was in severe pain at the beginning of the game. However, upon consumption of six diet soft drinks through the course of the game (approximately 1 g APM over 3 hours), the patient experienced substantial pain relief and markedly increased joint mobility.

Example 3

Multiple Sclerosis—Pain Alleviation

In one example of the analgesic properties of APM in combination with other analgesic agents in relieving pain associated with multiple sclerosis, four tablets each containing 19.5 milligrams of APM were ingested by a patient with multiple sclerosis. The dosage was repeated at 100–120 milligrams every six hours. Upon administration of the APM, the patient's need for opiates for relief from pain dropped by 50%: one-half tablet Percocet (Du Pont Pharmaceuticals, Wilmington, Del.; each tablet containing 5 mg oxycodone hydrochloride and 325 mg acetaminophen) taken 2–3 times a day rather than one tablet taken 4 times a day. By combining APM with the opiate analgesic, the required dosage of the opiate analgesic was decreased, thereby lessening the negative side effects of the opiate analgesic such as constipation experienced by the patient.

Example 4

Alleviation of Pain Associated with Injury

APM provided pain relief for a 48 year old female (non-arthritic) who injured her heel and associated tendons and ligaments to the arch of the foot while running along rough terrain. At 12 hours after the injury, the patient walked with a severe limp. Approximately 4 packets (about 0.15 grams) APM mixed in orange juice was given to the patient on an empty stomach. Approximately 50 minutes later, the patient participated in a one mile hike without noticeable limp. A second 4-packet dose in orange juice was administered 5 hours later. Eight hours after start of treatment, the patient was walking without pain. The following morning, there was tenderness to thumb pressure but no pain while walking. Thirty-six hours after treatment, there was no pain and very little tenderness.

Example 5

Alleviation of Pain Associated with Back Surgery

Enrolled in a blind study, an osteoarthritis patient was taking a study compound for pain relief. Prior to back surgery, the patient discontinued using the study compound, but postoperatively, he resumed taking five tablets of the study compound unprescribed three times a day. On Day 1 after surgery, the patient took only one prescribed p.r.n. pain tablet and discontinued use of a prescribed PCA pump narcotic pain reliever because he reported a lack of need. Despite continued access to prescribed pain relievers, the patient declined due to lack of need. The patient was walking on Day 1, went home on Day 3, and resumed normal routine without pain on Day 10. The blinded study compound was APM (19.5 milligrams per tablet).

Example 6

Myocardial Infarction—Pain Alleviation

Pain associated with myocardial infarction has been associated with platelet aggregation. Since the pain reliever effects of APM show properties in common with aspirin and other nonsteroidal anti-inflammatory agents, APM was further evaluated for possible anticoagulant properties.

A preliminary study of bleeding times in twelve normal subjects was performed. After baseline bleeding times were measured using the Simplate bleeding technique according to manufacturer's instructions (General Diagnostics, Organon Technica, Oklahoma City, Okla.), each subject ingested four tablets of aspartame (76 milligrams; 19 milligrams/tablet). Two hours after the oral ingestion of APM, repeat bleeding times were determined. The initial data demonstrated that a clinical response occurred in subjects with bleeding times of less than six minutes. Bleeding times longer than six minutes were thought to represent limits from commonly ingested dietary substances with properties similar to APM.

Since the preliminary data indicated possible clinical effects of APM on bleeding times, a double blind crossover study of 34 volunteers was conducted using the Simplate bleeding technique. All seventeen volunteers receiving placebo and seventeen receiving APM completed the study without complication. After a baseline bleeding time determination, each volunteer was given either four tablets of APM (76 milligrams; 19 milligrams/tablet) or four tablets of placebo.

Figure 9:
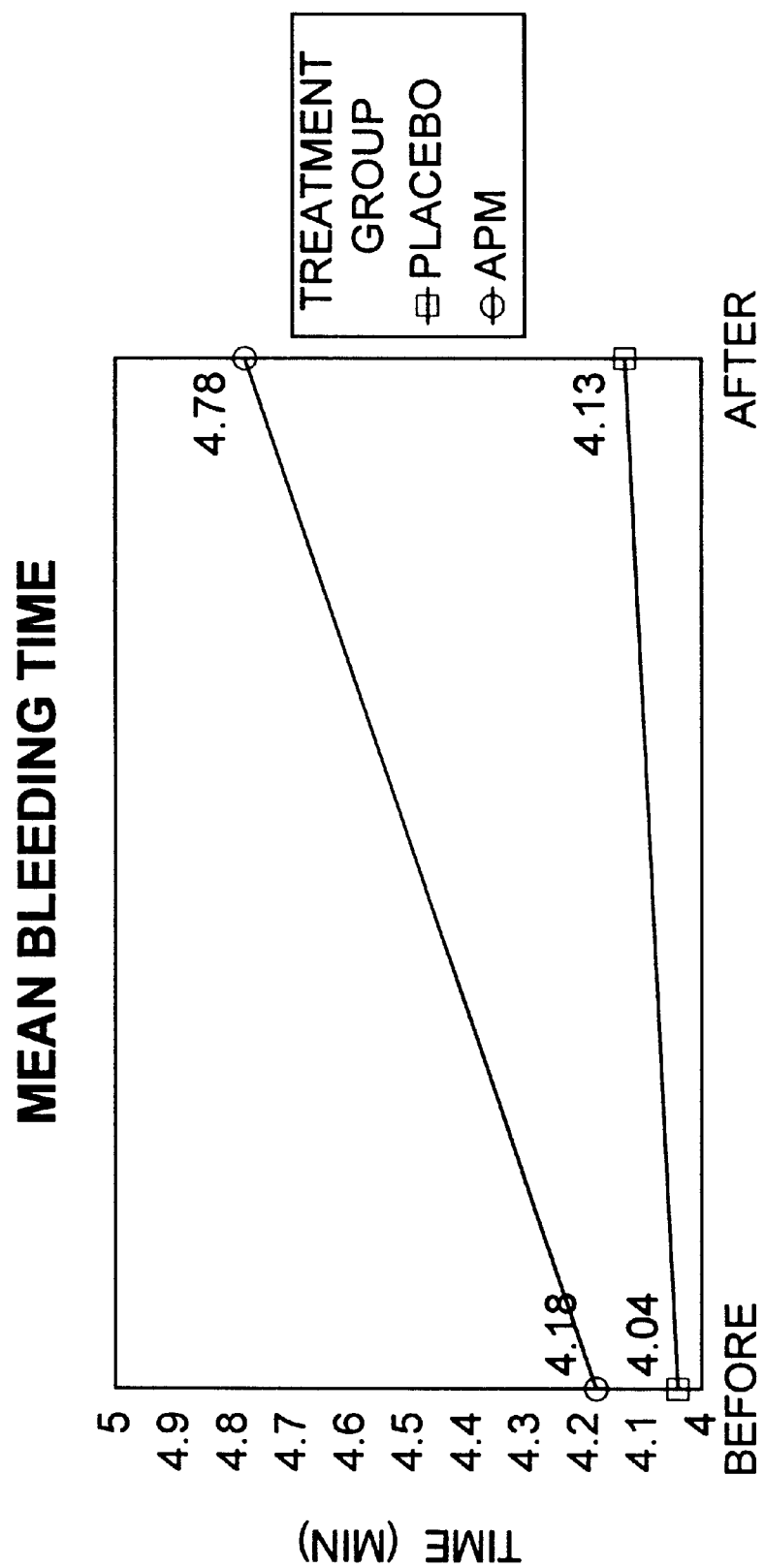
FIG. 9 is a graph depicting the average bleeding time before and after treatment with APM or placebo.
Figure 10:
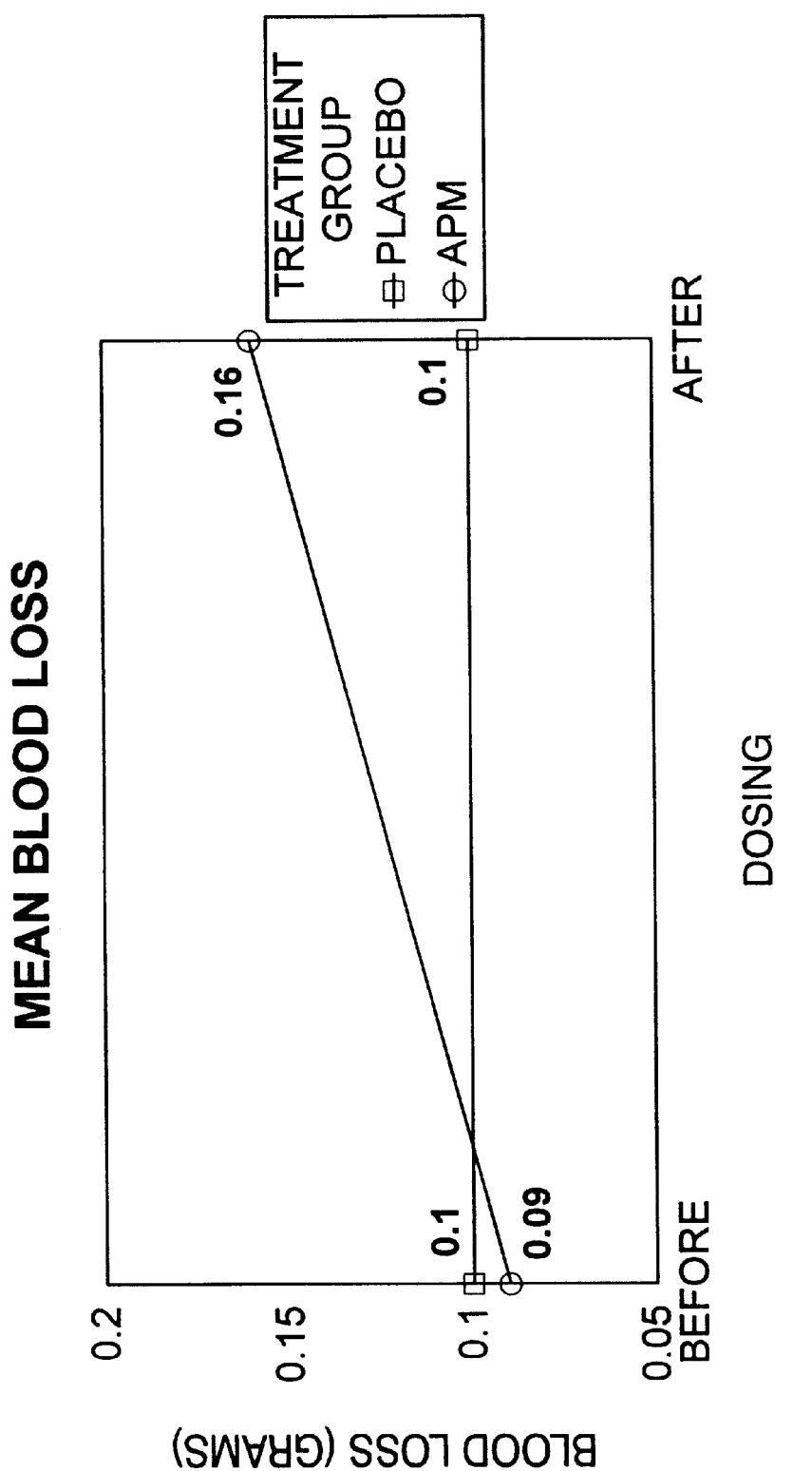
FIG. 10 is a graph depicting the average amount of blood loss before and after treatment with APM or placebo.

Two hours after dosing, the bleeding time was repeated. Each bleeding time determination used pre-weighed blotting paper to collect blood droplets. The blotting paper was weighed on an analytical balance after the bleeding stopped. The time required for the bleeding to stop was measured with a stop watch. The data for the APM and placebo volunteers are given in Table X and Table XI, respectively. The effects of APM on bleeding time is summarized in Table XII and in FIG. 9 and FIG. 10. The results show a slight prolongation of bleeding time with APM which is similar to the effect associated with aspirin. In the APM group, 13 volunteers had increased bleeding time, compared to 8 volunteers in the placebo group. By increasing bleeding time, APM may be used to control platelet aggregation and alleviate pain associated with myocardial infarction.

TABLE X

Bleeding Times Before and After APM

| | Before APM | | | | After APM | | | |
|---|---|---|---|---|---|---|---|---|
| Subject | Bleeding Time (min) | Pre-bleeding Wt (gram) | Post-bleeding Wt (gram) | Blood loss (gram) | Bleeding Time (min) | Pre-bleeding Wt (gram) | Post-bleeding Wt (gram) | Blood loss (gram) |
| 1 | 4.460 | 4.669 | 4.769 | 0.120 | 4.430 | 4.692 | 4.850 | 0.158 |
| 2 | 5.150 | 4.728 | 4.819 | 0.091 | 4.420 | 4.726 | 4.890 | 0.164 |
| 3 | 3.430 | 4.720 | 4.811 | 0.091 | 5.140 | 7.991 | 8.142 | 0.151 |
| 4 | 3.220 | 4.285 | 4.333 | 0.048 | 4.000 | 4.764 | 4.831 | 0.067 |
| 5 | 5.030 | 4.781 | 4.889 | 0.108 | 5.250 | 4.803 | 4.884 | 0.081 |
| 6 | 5.340 | 4.781 | 4.978 | 0.197 | 4.060 | 4.704 | 4.778 | 0.074 |
| 7 | 3.540 | 4.790 | 4.841 | 0.051 | 4.250 | 4.748 | 4.848 | 0.100 |
| 8 | 5.060 | 5.608 | 5.723 | 0.115 | 6.070 | 5.200 | 5.307 | 0.107 |
| 9 | 5.320 | 5.189 | 5.309 | 0.120 | 6.450 | 5.466 | 5.950 | 0.484 |
| 10 | 4.270 | 5.215 | 5.325 | 0.110 | 5.490 | 5.166 | 5.464 | 0.298 |
| 11 | 4.330 | 5.400 | 5.550 | 0.150 | 5.290 | 5.418 | 5.578 | 0.160 |
| 12 | 4.440 | 5.595 | 5.727 | 0.132 | 5.090 | 5.735 | 5.873 | 0.138 |
| 13 | 2.370 | 5.442 | 5.451 | 0.009 | 2.050 | 5.586 | 5.605 | 0.019 |
| 14 | 3.320 | 5.508 | 5.548 | 0.040 | 3.380 | 5.361 | 5.372 | 0.011 |
| 15 | 3.380 | 6.015 | 6.040 | 0.025 | 4.060 | 5.792 | 5.825 | 0.033 |
| 16 | 4.220 | 5.532 | 5.640 | 0.108 | 5.020 | 5.608 | 5.819 | 0.211 |
| 17 | 4.220 | 8.053 | 8.087 | 0.034 | 6.270 | 7.971 | 8.432 | 0.461 |
| Average | 4.182 | | | 0.091 | 4.748 | | | 0.160 |

TABLE XI

Bleeding Times Before and After Placebo

| | Before Placebo | | | | After Placebo | | | |
|---|---|---|---|---|---|---|---|---|
| Subject | Bleeding Time (min) | Pre-bleeding Wt (gram) | Post-bleeding Wt (gram) | Blood loss (gram) | Bleeding Time (min) | Pre-bleeding Wt (gram) | Post-bleeding Wt (gram) | Blood loss (gram) |
| 1 | 3.270 | 4.690 | 4.735 | 0.045 | 4.530 | 4.656 | 4.755 | 0.099 |
| 2 | 4.480 | 4.735 | 4.858 | 0.123 | 3.270 | 4.731 | 4.793 | 0.062 |
| 3 | 3.550 | 4.707 | 4.771 | 0.064 | 3.360 | 4.691 | 4.726 | 0.035 |
| 4 | 4.300 | 5.404 | 5.461 | 0.057 | 4.040 | 5.927 | 5.960 | 0.033 |
| 5 | 4.510 | 4.766 | 4.952 | 0.186 | 6.440 | 4.731 | 5.171 | 0.545[a] |
| | | | | | | 3.747 | 3.852 | |
| 6 | 4.560 | 5.545 | 5.643 | 0.098 | 4.180 | 4.723 | 4.788 | 0.065 |
| 7 | 5.230 | 5.480 | 5.609 | 0.129 | 5.180 | 5.658 | 5.789 | 0.131 |
| 8 | 4.500 | 5.403 | 5.479 | 0.076 | 4.040 | 5.366 | 5.426 | 0.060 |
| 9 | 3.160 | 5.325 | 5.417 | 0.092 | 3.380 | 5.354 | 5.505 | 0.151 |
| 10 | 3.420 | 5.418 | 5.515 | 0.097 | 3.430 | 5.251 | 5.388 | 0.137 |
| 11 | 4.270 | 5.375 | 5.510 | 0.135 | 3.440 | 5.434 | 5.500 | 0.066 |
| 12 | 2.470 | 5.328 | 5.380 | 0.052 | 2.220 | | | 0.000[b] |
| 13 | 3.180 | 5.208 | 5.284 | 0.076 | 5.120 | 5.473 | 5.572 | 0.099 |
| 14 | 4.280 | 5.648 | 5.696 | 0.048 | 4.580 | 5.424 | 5.519 | 0.095 |
| 15 | 3.490 | 5.917 | 5.974 | 0.057 | 5.450 | 6.066 | 6.148 | 0.082 |

TABLE XI-continued

Bleeding Times Before and After Placebo

| | Before Placebo | | | | After Placebo | | | |
|---|---|---|---|---|---|---|---|---|
| Subject | Bleeding Time (min) | Pre-bleeding Wt (gram) | Post-bleeding Wt (gram) | Blood loss (gram) | Bleeding Time (min) | Pre-bleeding Wt (gram) | Post-bleeding Wt (gram) | Blood loss (gram) |
| 16 | 5.070 | 5.857 | 6.035 | 0.178 | 4.200 | 5.897 | 5.971 | 0.074 |
| 17 | 4.320 | 7.962 | 8.145 | 0.183 | 3.350 | 8.047 | 8.149 | 0.102 |
| Average | 4.004 | | | 0.100 | 4.130 | | | 0.080 |

[a]Two separate blotter papers used to absorb volunteer's blood; since total blood loss was outside of normal range, blood loss value not included in mean analysis.
[b]Volunteer did not bleed.

TABLE XII

Summary of Bleeding Time by Event and Mean Values

| Treatment Group | Bleeding Time | | Number of Patients | |
|---|---|---|---|---|
| | Before | After | Increased Bleeding Time | Decreased Bleeding Time |
| APM | 4.18 | 4.78 | 13 | 4 |
| Placebo | 4.04 | 4.13 | 8 | 9 |

Example 7

Use of APM as a Veterinary Pain Reliever

A fifteen year old German shepherd dog experiencing osteoarthritic symptoms was given 5–10 tablets APM (95–190 milligrams; 19 milligrams/tablet) twice a day. Three days later, the dog had resumed normal activities. When the treatment was subsequently discontinued, the dog again exhibited osteoarthritic symptoms and lack of appetite. Treatment with APM was resumed, and the dog again resumed normal activity.

We claim:

1. An animal feed comprising at least one composition of the formula:

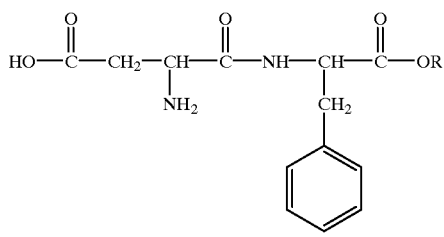

wherein R is H or an alkyl containing 1 to 6 carbons, in a sufficient amount per serving to stimulate the appetite of an animal consuming at least one serving per day of said feed.

2. The animal feed of claim 1, wherein said sufficient amount is 190–380 milligrams per serving.

3. The animal feed of claim 1, wherein said sufficient amount is 95–189 milligrams per serving.

4. The animal feed of claim 1, wherein said sufficient amount is 3–94 milligrams per serving.

5. The animal feed of claims 1, 2, 3 or 4, wherein said animal feed is suitable for dogs.

6. A dog food suitable for dogs weighing from about 31.7 to about 50 kilograms, having a daily serving amount for said dogs, said daily serving amount comprising about 95 to about 360 milligrams of:

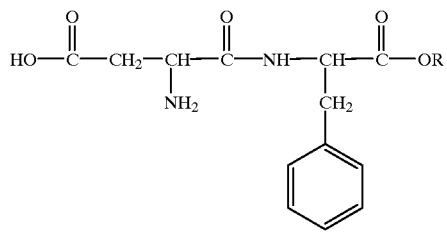

wherein R is H or an alkyl containing 1 to 6 carbons.

7. A dog food suitable for dogs weighing from about 13.6 to about 31.3 kilograms, having a daily serving amount for said dogs, said daily serving amount comprising about 26 to about 360 milligrams of:

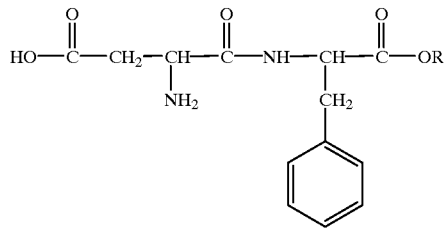

wherein R is H or an alkyl containing 1 to 6 carbons.

8. A dog food suitable for dogs weighing from about 6.8 to about 13.2 kilograms, having a daily serving amount for said dogs, said daily serving amount comprising about 13 to about 160 milligrams of:

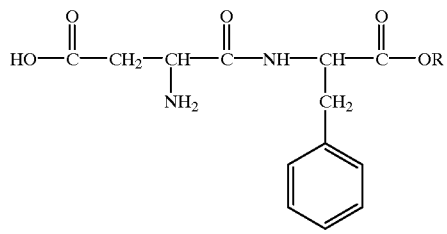

wherein R is H or an alkyl containing 1 to 6 carbons.

9. A dog food suitable for dogs weighing from about 3.2 to about 6.4 kilograms, having a daily serving amount for said dogs, said daily serving amount comprising about 6 to about 80 milligrams of:

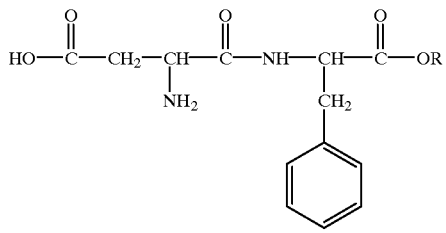

wherein R is H or an alkyl containing 1 to 6 carbons.

10. A dog food suitable for dogs weighing from about 1.4 to about 2.8 kilograms, having a daily serving amount for said dogs, said daily serving amount comprising about 3 to about 32 milligrams of:

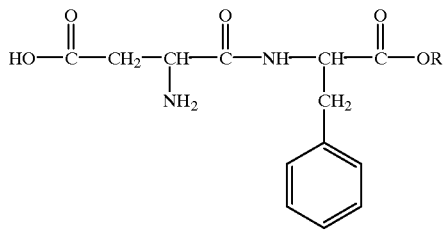

wherein R is H or an alkyl containing 1 to 6 carbons.

11. A dietary supplement for enhancing appetite in unit dosage form for administration to a vertebrate animal, comprising at least one composition of the formula:

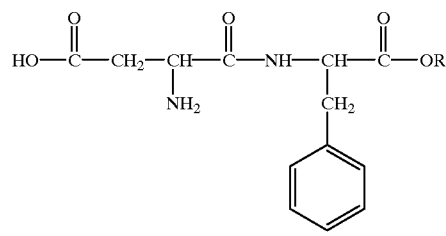

wherein R is H or an alkyl containing 1 to 6 carbons.

12. The dietary supplement of claim 11, wherein said unit dosage comprising from about 2 to about 6 milligrams per kilogram body weight of said vertebrate animal.

13. The dietary supplement of claim 11, wherein said unit dosage comprising from about 3.5 to about 18 milligrams per kilogram body weight of said vertebrate animal.

14. The dietary supplement of claim 11, wherein said unit dosage comprising from about 1 to about 36 milligrams per kilogram body weight of said vertebrate animal.

15. A method for stimulating the appetite of an animal by adding to an orally ingestible substance an appetite-stimulating amount of:

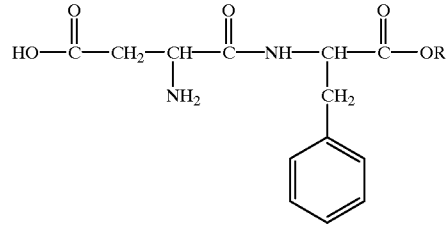

wherein R is H or an alkyl containing 1 to 6 carbons.

16. The method of claim 15, wherein said substance is food.

17. The method of claim 15, wherein said substance is a liquid or beverage.

18. The method of claim 15, wherein said appetite-stimulating amount is a solution, spray, powder, crystal, capsule, tablet, or microencapsulated or entrapped in liposomes.

* * * * *